United States Patent [19]

Clemens et al.

[11] Patent Number: 4,526,568
[45] Date of Patent: Jul. 2, 1985

[54] DIAGNOSTIC METHOD AND APPARATUS FOR CLAMPING BLOOD GLUCOSE CONCENTRATION

[75] Inventors: A. H. Clemens, Elkhart, Ind.; David L. Hough, Edwardsburg, Mich.

[73] Assignee: Miles Laboratories, Inc., Elkhart, Ind.

[21] Appl. No.: 426,983

[22] Filed: Sep. 29, 1982

[51] Int. Cl.³ .......................... A61M 5/00; A61B 5/00
[52] U.S. Cl. .......................................... 604/4; 604/28; 604/50; 604/31; 604/66; 604/67
[58] Field of Search .................. 604/4, 28, 50, 27, 30, 604/31, 51, 52, 56, 65-67; 128/DIG. 13

[56] References Cited

U.S. PATENT DOCUMENTS

| | | | |
|---|---|---|---|
| 3,837,339 | 9/1974 | Aisenberg et al. | 604/66 |
| 4,055,175 | 10/1977 | Clemens et al. | 604/66 |
| 4,206,755 | 6/1980 | Klein | 604/28 |
| 4,245,634 | 1/1981 | Albisser et al. | 604/66 |

Primary Examiner—Richard J. Apley
Assistant Examiner—Gregory Beaucage
Attorney, Agent, or Firm—Roger N. Coe

[57] ABSTRACT

A diagnostic apparatus and method for clamping the blood glucose concentration of a subject at any one of a plurality of levels. A desired clamping level (BC) is selected and the value of the present blood glucose concentration, corrected to fit a least squares regression lines (GY) in the bloodstream of the subject is periodically determined. Dextrose is introduced into the bloodstream of the subject at a rate (DR) derived in accordance with $$DR = WT\left[\left(\frac{BC - GY}{3 + M}\right)KS + RC\right]$$

wherein:
DR = dextrose infusion rate for clamp (mg/min)
WT = body weight (kg)
BC = desired clamp level (mg %)
GY = present blood glucose level, corrected to fit a least squares regression line (mg %)
M = slope of the least squares regression line fit for the last five glucose values
KS = constant to allow adjustment for differences in metabolism $$RC = .9RC_{Last} + .1\left(\frac{DR_{Last}}{WT}\right)$$

(Glucose utilization in mg/kg/min).

3 Claims, 7 Drawing Figures

DIAGNOSTIC METHOD AND APPARATUS FOR CLAMPING BLOOD GLUCOSE CONCENTRATION

BACKGROUND OF THE INVENTION

The present invention relates to a diagnostic method and apparatus for clamping the blood glucose concentration of a subject at any one of a plurality of levels.

The glucose clamping technique has been envisioned as a valuable diagnostic tool for the early identification of derangements in glucose metabolism in human beings. During glucose clamping, the normal glucose insulin relationship is interrupted by placing the patient's blood glucose concentration under the investigator's control. Thus, by clamping a patient's blood glucose concentration at a hyperglycemic level, with no additional exogenous insulin, the pancreatic beta cell response to glucose may be observed. Likewise, by holding the patient's blood glucose concentration at a normoglycemic level, with programmed insulin infusion and feedback controlled infusion of dextrose, the sensitivity of body tissues to insulin may be studied.

The diagnostic technique of glucose clamping therefore differs from the aim of therapeutic techniques of glucose monitoring systems such as that disclosed in U.S. Pat. No. 4,151,845 since such systems act as a life support system and aid in the body's inability to maintain a normoglycemic level.

The glucose clamping technique also differs from oral glucose and insulin tolerance tests since the hyperglycemic clamp, unlike the oral glucose tolerance test permits the time course of glucose metabolism by the body to be quantified and separated into the early and late phases of insulin secretion. The normoglycemic clamp with insulin infusion, eliminates the possible danger of hypoglycemic excursions present with insulin tolerance tests. The complex physiological responses to hypoglycemia are also avoided, thus providing a more reliable estimate of tissue sensitivity to insulin.

While the glucose clamping technique has been recognized as a potentially valuable diagnostic tool, no automatic method or system for utilizing same has been reliably carried out.

While various algorithms have been utilized for carrying out such a technique, these have not been sufficiently reliable to achieve the desired results of an automatic method and apparatus for glucose clamping.

SUMMARY OF THE INVENTION

The main object of the present invention is to provide a method and an apparatus for achieving glucose clamping wherein the glucose concentration can be periodically determined and dextrose can be introduced into the bloodstream of the subject under investigation in a manner so as to maintain a desired clamp level within close tolerances.

This and other objects of the present invention are achieved in accordance with the present invention by the use of a insulin and dextrose infusion apparatus of the type disclosed in U.S. Pat. No. 4,151,845, and whose disclosure is incorporated herein by reference, and wherein the desired clamp level is maintained by introducing dextrose at rates derived in accordance with:

$$DR = WT\left[\left(\frac{BC - GY}{3 + M}\right) KS + RC\right]$$

wherein:
DR = dextrose infusion rate for clamp in milligrams per minute (mg/min)
WT = body weight in kilograms (kg)
BC = desired clamp level in milligram percent (mg %)
GY = present blood glucose level, corrected to fit a least squares regression line (mg %)
M = slope of the least squares regression line fit for the last five glucose values
KS = constant to allow adjustment for differences in metabolism $$RC = .9RC_{Last} + .1\left(\frac{DR_{Last}}{WT}\right)$$

(Glucose utilization in mg/kg/min).

The above-referenced algorithm for controlling the rate of dextrose differs from those suggested in the prior art by the fact that it does not assume normal insulin response by the body tissue and thus is able to measure sensitivity of the tissue to insulin.

Further in accordance with the present invention, insulin is introduced into the bloodstream of the subject at a rate:

$$IR = RL \times WT$$

wherein:
IR = insulin infusion rate in milliunits per minute (mU/min)
RL = selected rate of insulin loading per kg of body weight.

Furthermore, in accordance with the invention, the insulin response of the person being analyzed can be obtained by introducing insulin into the bloodstream at a plurality of selected different fixed rates IR for a given normoglycemic clamp level. The steady state value of the dextrose infusion rate DR for each insulin infusion rate can be plotted as a series of curves. It is the shift in the curve that would be indicative of the insulin response.

It has been found that maturity onset diabetes exhibits a change in tissue sensitivity to insulin. The clamp according to the present invention will be able to determine variations in tissue sensitivity and enable doctors to diagnose maturity onset diabetes while it is still in its initial stages.

Other and further objects, advantages and features of the invention will be apparent to those skilled in the art from the following detailed description thereof, taken in conjunction with the accompanying drawings, wherein:

BRIEF DESCRIPTION OF THE DRAWINGS

FIG. 6 shows curves for a hyperglycemic clamp with no infusion of exogenous insulin.

DETAILED DESCRIPTION OF THE INVENTION

Figure 1:
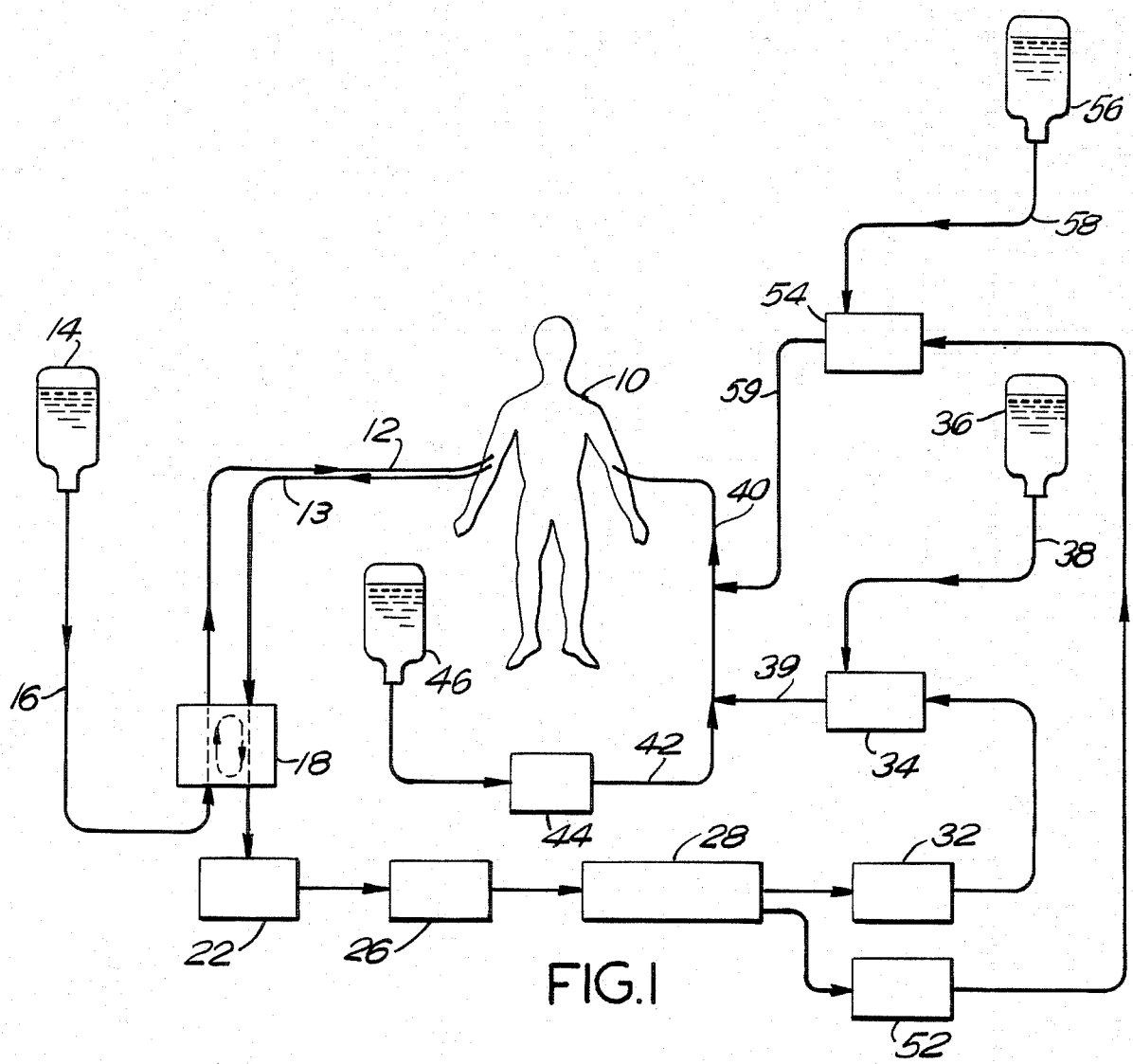
FIG. 1 is a schematic view of an apparatus according to the present invention.

Referring now to FIG. 1, the apparatus according to the present invention and which is used for the method according to the present invention is disclosed in schematic form.

Blood is removed from the blood stream of subject 10 by suitable means, such as through a double lumen catheter (not shown), which also introduces an anticoagulant such as heparin, in line 12, which is mixed with the blood as it leaves the subject, thereby diluting the blood passing through line 13. The anticoagulant is stored in reservoir 14 and is pumped to the catheter through lines 16 and 12 by suitable means, such as peristaltic pump 18, which also pumps diluted blood from the catheter through line 13 in the opposite direction. Pump 18 runs continuously to drive the diluted blood from line 13 into glucose analyzer 22.

Glucose analyzer 22 can take a variety of forms. For example, using a colorimeter approach, diluted blood enters analyzer 22 and is diluted further with a physiological saline solution before being segmented with air into discrete bits to be dialyzed against a glucose oxidase-peroxidase-chromagen reagent. The presence of blood glucose specifically alters the color of the reagent and the optical density of the resulting color is measured by a colorimeter which generates a corresponding output signal. The resulting signal is then fed to analog-to-digital converter 26 which prepares the input signal for digital computer 28.

In a preferred embodiment glucose analyzer 22 is a membrane type polarographic assembly which measures the glucose level of the diluted blood and generates a corresponding signal which is supplied to analog-to-digital converter 26 which prepares the input signal for digital computer 28. Suitable membrane type polarographic apparatus is described, for example, U.S. Pat. No. 4,092,233. This membrane contains glucose oxidase which converts glucose to hydrogen peroxide which is detected in the polarographic assembly by a difference in electrical potential.

Analog-to-digital converter 26 feeds the digital input signal corresponding to the blood glucose level to computer 28, which is programmed according to an algorithm which will be discussed later. Responsive to the signals from analyzer 22, the computer determines the infusion rate of dextrose for the subject by use of the algorithm programmed into the computer. Once the infusion rate required by the clamp has been determined, digital signals are fed from computer 28 to pump interface 32 which controls the infusion pumping which will now be described. Pump 54 connected to interface 52 receives dextrose from reservoir 56 by way of line 58 and feeds the dextrose into lines 59 and 40. Line 42 receives saline solution from pump 44, which draws said solution from reservoir 46. Accordingly, dextrose from reservoir 56 is mixed with saline solution as it is fed into line 40, and the resulting solution is introduced into the blood stream of subject 10 through a suitable catheter (not shown). A closed loop is therefore provided which includes subject 10.

It will be understood that while the use of a digital computer is preferred, converter 26 and computer 28 can be replaced by an analog computer, if desired. Pump 54 would then be driven in analog fashion rather than in digital fashion.

As will be apparent, the regulation afforded by the structure described with reference to FIG. 1 depends on computer algorithm programmable into computer 28. Ideally, the algorithm should be capable of interpreting requirements for dextrose to the point where the blood glucose concentration of a subject is maintained substantially constant at a BC level which is desired for the diagnostic test In the normoglycemic clamping method, it is also desirable to infuse insulin at a fixed rate into the subject 10. In this event, the computer 28 can also set the desired fixed rate based on parameters already entered in for determining the dextrose infusion rate for the clamp, as will be explained hereinafter, and the computer by means of a pump interface 32 controls insulin pump 34 which receives insulin from reservoir 36 via line 38 and which pumps insulin into line 40 via line 39.

Development of an algorithm suitable for use with this apparatus and tailored to glucose clamping was developed on the basis of the ability of the algorithm to respond quickly to changes in the glucose concentration of a subject and to maintain the clamp within close tolerances. The key factor in the development of the algorithm was the fact that it does not assume normal insulin response by the body tissue, but takes into account the fact that there is tissue sensitivity to insulin and as a result it is this response that must be determinable.

The glucose clamping control algorithm is as follows:

$$DR = WT\left[\left(\frac{BC - GY}{3 + M}\right) KS + RC\right]$$

wherein:
DR = dextrose infusion rate for clamp (mg/min)
WT = body weight (kg)
BC = desired clamp level (mg %)
GY = present blood glucose level corrected to fit a least squares regression line (mg %)
M = slope of the least squares regression line fit for the last five glucose values
KS = constant to allow adjustment for differences in metabolism $$RC = .9RC_{Last} + .1\left(\frac{DR_{Last}}{WT}\right)$$

(Glucose utilization in mg/kg/min).

In addition, the infusion of insulin at a fixed rate is controlled in the following manner:

$$IR = RL \times WT$$

wherein:
IR = insulin infusion rate (mU/min)
RL = selected rate of insulin loading per kg of body weight. Typically, RL is in the range of between 0 and 10 milliunits per kilogram per minute.

It was experimentally determined that the constant KS is usually between 1 and 2. The data obtained from clamping studies is set forth the following examples and shown in FIGS. 2-6 which illustrate the glucose levels at five minute intervals with an average value for the dextrose infusion rate at 10 minute intervals. The blood glucose values prior to achieving the clamp values were omitted from the drawings.

The glucose clamping diagnostic method can yield valuable information concerning the state of glucose metabolism in a subject. That information can be divided into that derived from hyperglycemic and normoglycemic clamps. Hyperglycemic clamps, with no infusion of exogenous insulin, produces information concerning the pancreatic beta cell response to high blood glucose levels. Normoglycemic clamps, with programmed insulin infusion rates and feedback controlled infusion of dextrose, are useful for quantitating tissue sensitivity to insulin.

The diagnostic tests conducted with the glucose clamping algorithm utilized computer controlled infusion of dextrose in order to maintain blood glucose concentrations at a predetermined clamp level. The dextrose infusion rate DR in mg/kg/min required to maintain the clamp and the last minutes blood glucose value were available to the operator. In the case of a normoglycemic clamp with a fixed insulin infusion rate, the value DR can be used to estimate glucose metabolism which is understood as being a valid estimate when the dextrose infusion rate has reached a steady state value as a function of time and the glucose entering the blood is from the exogenous source only. This condition exists when the supply of endogenously produced glucose entering the blood is completely surpressed. It has been shown that such occurs at plasma insulin concentrations at or above 50–60 mU/mL. According to the diagnostic method of the present invention, at insulin infusion rates of 0.5, 2.0 and 5.0 mU/kg/min, steady state insulin concentrations of $58+4$, $195\pm9$ and $570\pm17$ mU/mL, respectively, were achieved within 30 minutes.

EXAMPLES RESULTS OF NORMOGLYCEMIC CLAMPS

Figure 2:
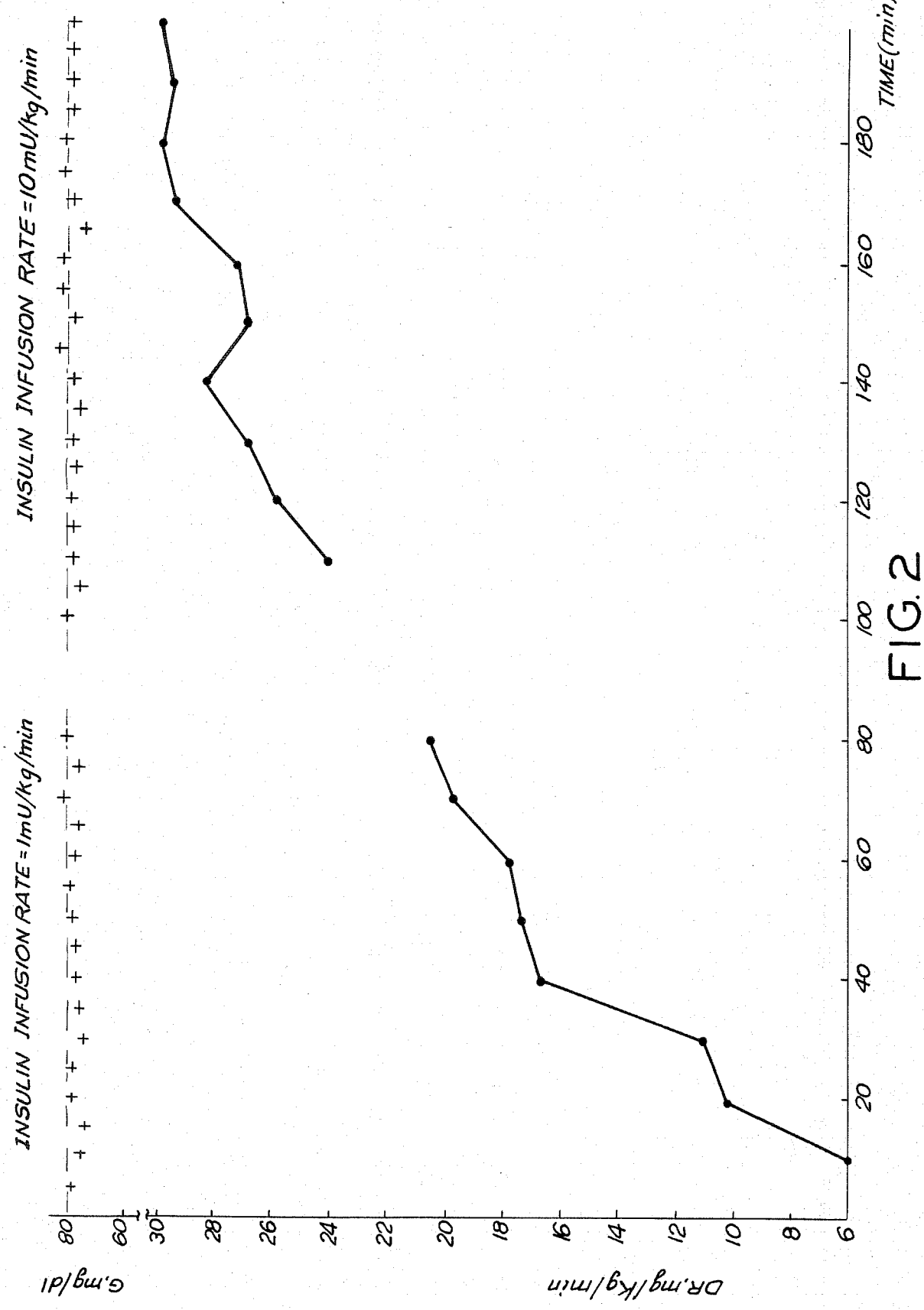
FIGS. 2-6 show families of curves representing operation of the apparatus and method according to the present invention at various clamp levels at different insulin infusion rates and showing the dextrose infusion rate versus time.

FIG. 2 demonstrates a normoglycemic glucose clamp (80 mg/dL) on a normal, 8 kilogram (kg) male dog with insulin infusion rates of 1 and 10 mU/kg/min. The upper plot is the dog's blood glucose value at five minute intervals and the bottom plot is the DR value, the dextrose infusion in milligrams/kilogram/minute (mg/kg/min) required to maintain the clamp. The clamp was maintained for 80 min at the low insulin infusion rate and 200 min at the high infusion rate. The glucose value was maintained at $76.8\pm2.5$ milligrams/deciliter (mg/dL) during the low insulin infusion and $78.4\pm3.2$ mg/dL during the high insulin infusion. The DR value achieved steady state at a value of 29.5 mg/kg/min at approximately 170 min into the clamp.

Figure 3:
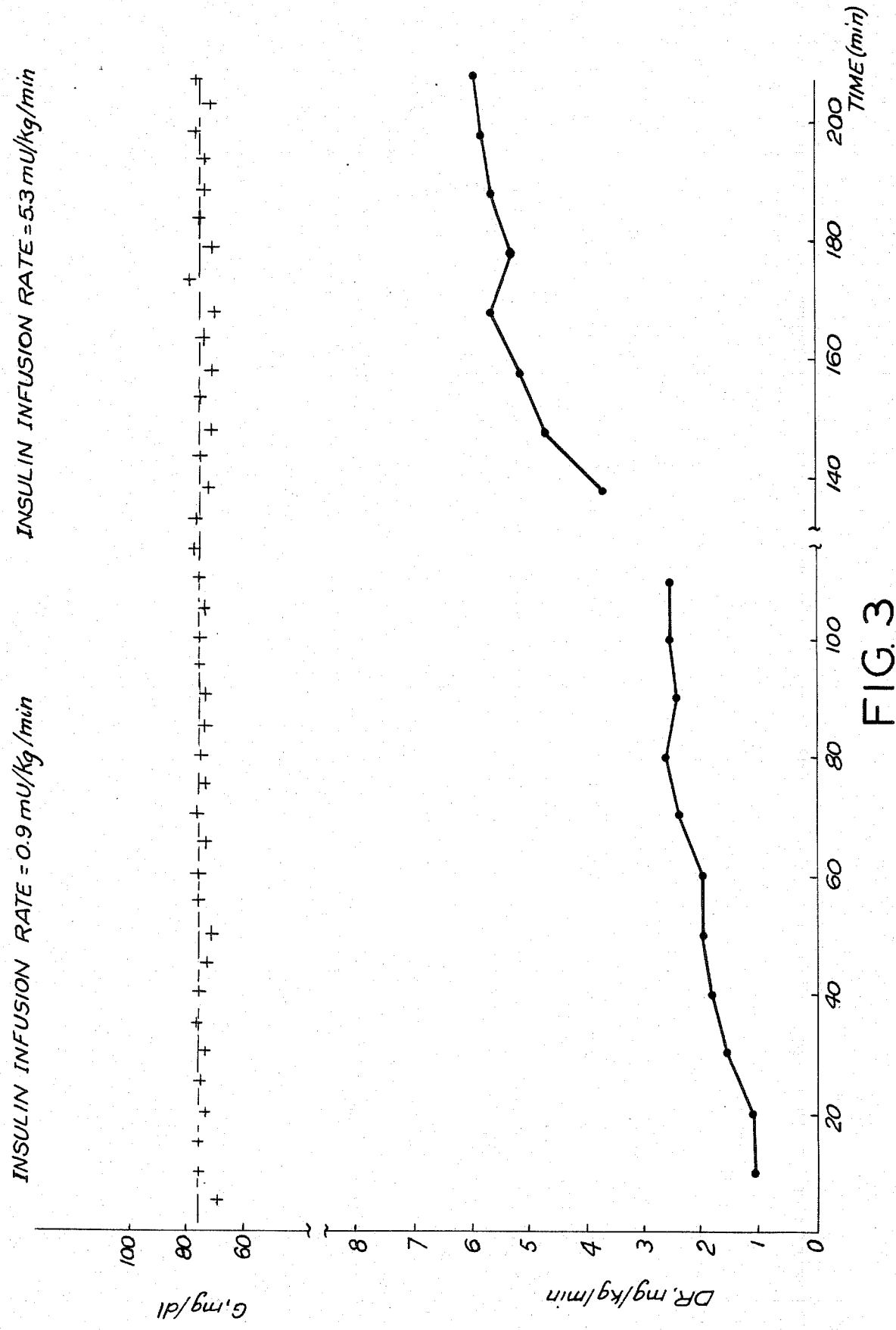
Figure 4:
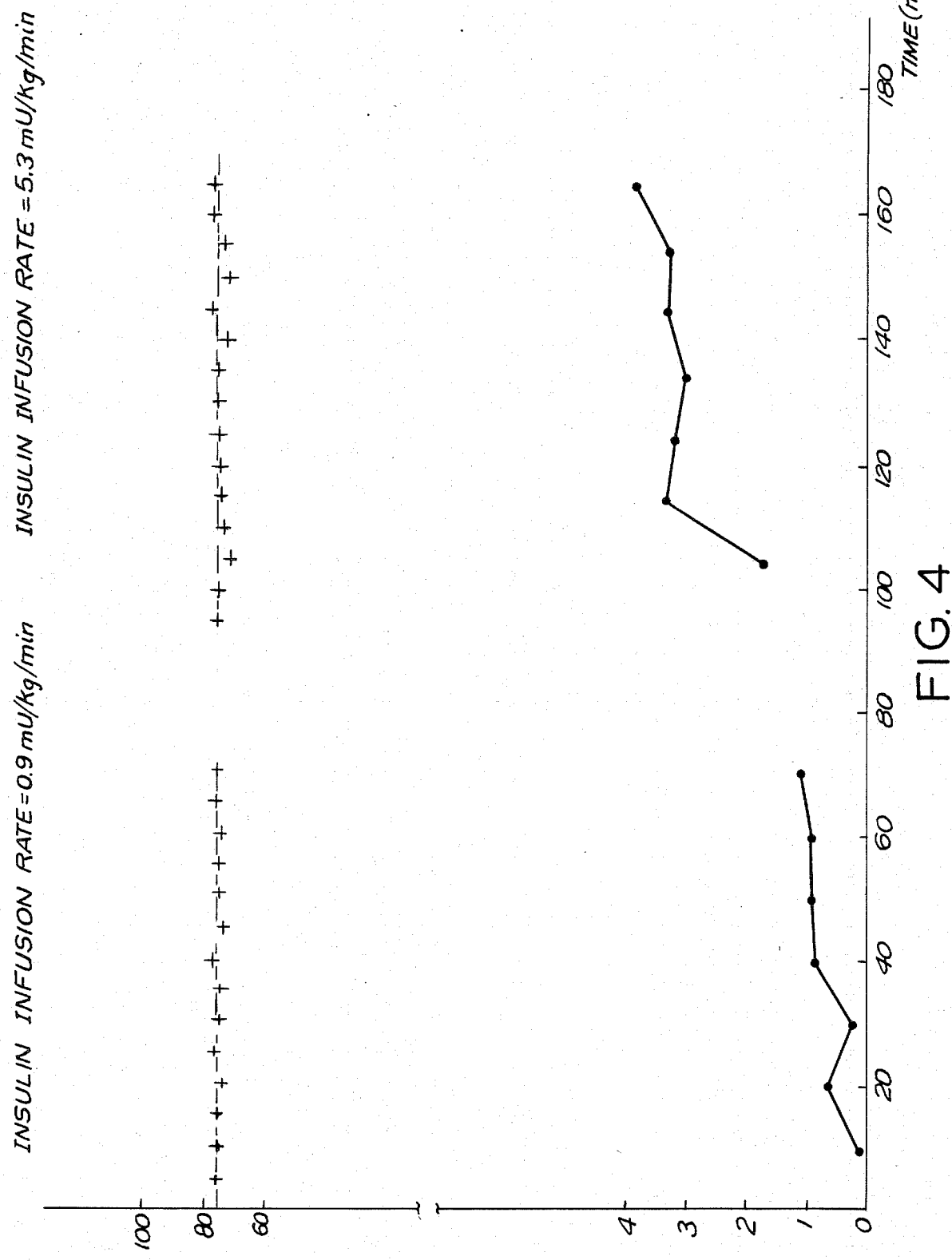
Figure 5:
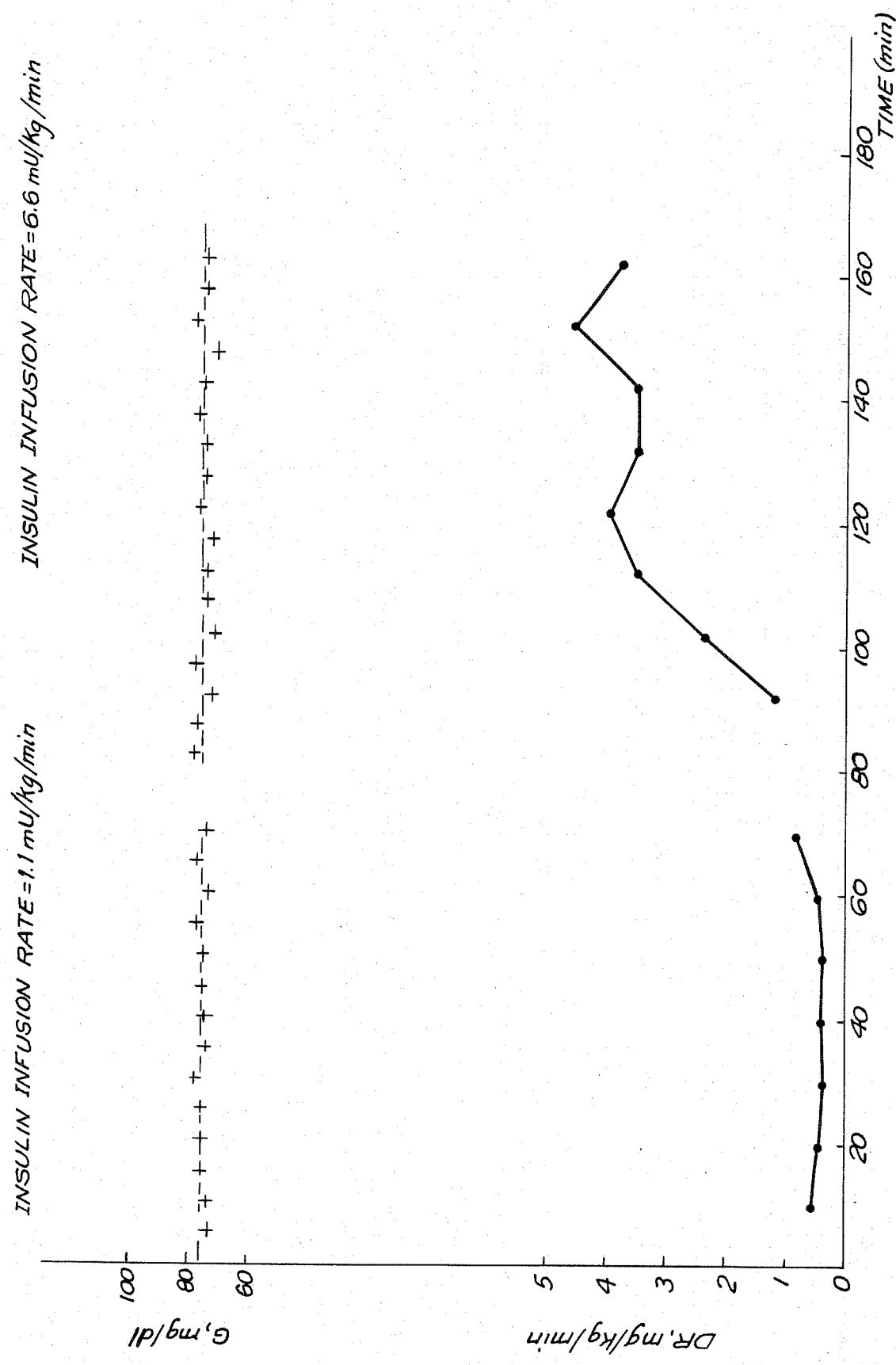
Figure 6:
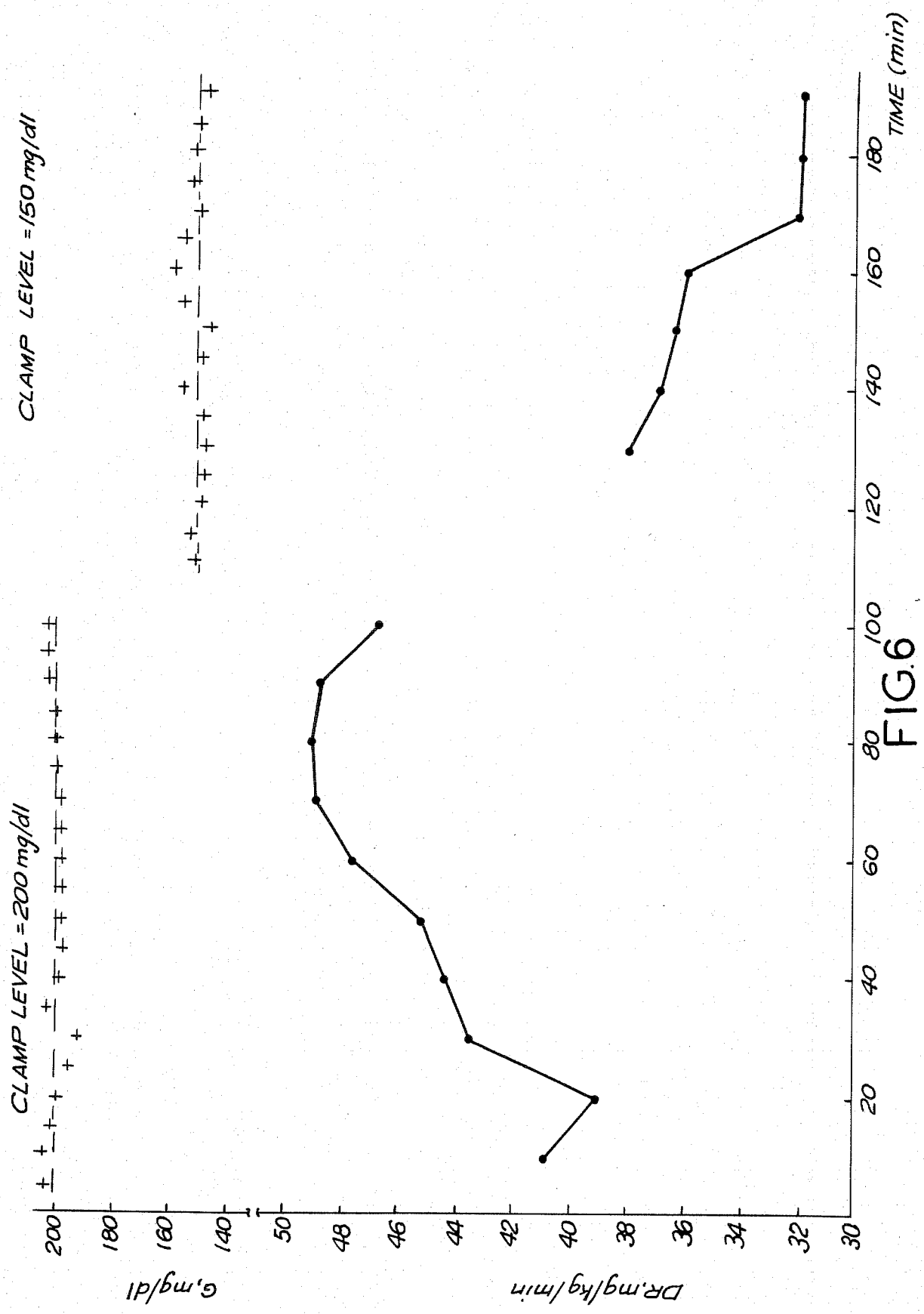

Results of normoglycemic clamps on humans are shown in FIGS. 3–5. FIGS. 3 and 4 represent normal individuals clamped at a glucose value of 75 mg/dL. The curves on the left in these figures represent an insulin infusion rate of 0.9 mU/kg/min. The curves on the right represent an insulin infusion rate of 5.3 mU/kg/min. The individual of FIG. 3, a normal female, showed a mean blood glucose value of $74.2\pm2.3$ mg/dL and a steady state dextrose infusion rate of 2.5 mg/kg/min at approximately 80 min into the low insulin infusion rate clamp. The clamp with the high insulin infusion rate showed a mean blood glucose value of $73.9\pm2.0$ mg/dL and a steady state dextrose infusion rate of 6.0 mg/kg/min at approximately 170 min into the clamp.

The individual of FIG. 4, a normal, obese female demonstrated a mean blood glucose value of $74.2\pm1.9$ mg/dL and a dextrose infusion rate of 1.0 mg/kg/min at approximately 40 min into the low insulin infusion rate clamp. At the high insulin infusion rate, the mean blood glucose value is $74.8\pm1.2$ mg/dL and the dextrose infusion rate is 3.3 mg/kg/min at approximately 110 min into the clamp.

The individual of FIG. 5 was a female, maturity onset diabetic. The insulin infusion rates utilized for this subject are slightly greater than those shown in FIGS. 3 and 4 (1.1, 6.6 mU/kg/min). At the low insulin infusion rate, this individual demonstrated a mean blood glucose value of $75.0\pm2.0$ mg/dL and a steady state dextrose infusion rate of approximately 0.5 mg/kg/min immediately into the clamp. At the high insulin infusion rate, the mean blood glucose value is $73.9\pm1.5$ mg/dL and the dextrose infusion rate was approximately 3.8 mg/kg/min at 120 min into the clamp.

Based on these data, comparisons can be made between the patterns noted for the individuals of FIGS. 3–5. The low sensitivity to insulin shown by the subject of FIG. 4 resembles that shown by the subject of FIG. 5, a known maturity onset diabetic, and may be a sign of an early derangement in glucose metabolism.

Results of Hyperglycemic Clamps

In contrast to the maturity onset type, juvenile onset diabetes is characterized by lack of insulin secretion in response to a dextrose challenge due to defective or missing pancreatic beta cells. Hyperglycemic clamping of an individuals blood glucose concentration, with no infusion of exogenous insulin, should permit an assessment of beta cell function FIG. 6 demonstrates a normal, 8 kg dog clamped at hyperglycemic levels of 200 and 150 mg/dL using the Glucose Clamping algorithm. The left side of the figure is a 200 mg/dL clamp which is conducted for 100 min. The mean blood glucose value is $196.7\pm2.9$ mg/dL. The DR value showed a steady increase throughout this period and reached a plateau at approximately 49 mg/kg/min. This plateau probably represents the steady state response of the pancreatic beta cells to the hyperglycemic blood glucose value. Beyond this point, the amount of dextrose required to maintain the clamp shows a decrease and may indicate a decrease in glucose metabolism. This decrease continues when the clamp level is lowered to 150 mg/dL where it is maintained for 80 min at a mean blood glucose value of $150.7\pm4.4$ mg/dL.

The ability to maintain a "tight" clamp, that is, one with a minimum deviation from the target value is needed in order to avoid stimulation of unwanted physiological responses. The mean blood glucose value normoglycemic clamps on humans is 74.3 mg/dL with a mean standard deviation of $\pm1.8$ mg/dL. The Glucose Clamping algorithm permits maintenance of a glucose clamp with less deviation from the target value than was previously possible.

The glucose clamping method and apparatus according to the present invention will contribute to a better understanding of disorders in the glucose hemostasis in man. The use of the method and apparatus according to the present invention will permit early recognition of a metabolic derangement prior to full manifestation of maturity on set diabeties.

Figure 7:
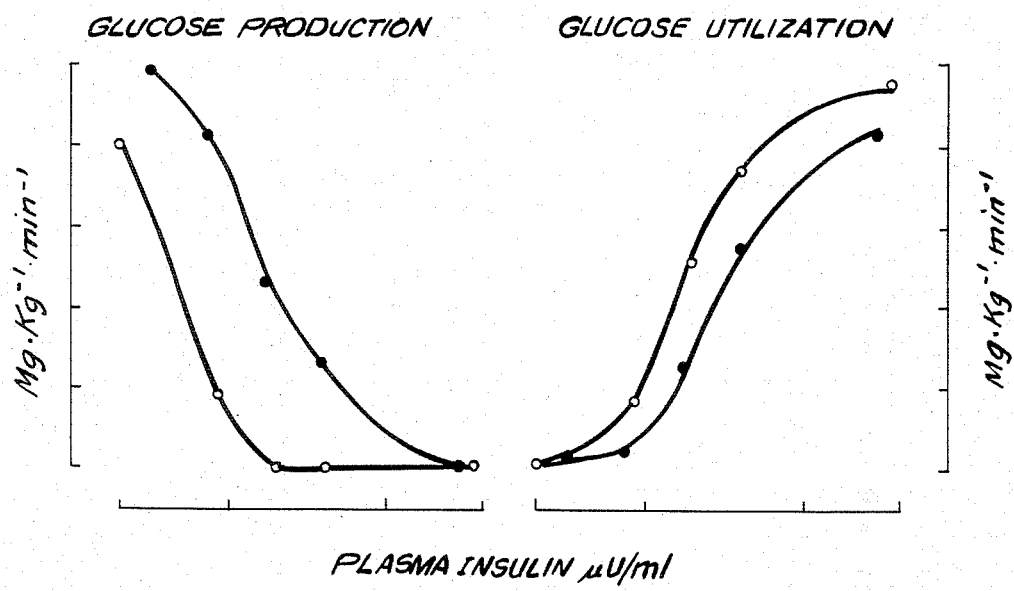
FIG. 7 illustrates the shift in the dextrose utilization versus insulin infusion rate indicative of the insulin response of a person being analyzed.

After studies of persons who are known to be maturity on set diabetics and those persons that are normal are completed, diagnosticians will be able to compile a data base classified according to the magnitude of the metabolic derangement. In accordance with the curves shown in FIG. 7, the formation of the shift in the glucose utilization, curve versus increase in plasma insulin will enable the glucose clamping method and apparatus according to the present invention to be used as a screening procedure for the detection of early stages of maturity on set diabetes. Since maturity on set diabetes is usually characterized by a loss of tissue sensitivity and responsiveness to insulin due to a proposed abnormality of the insulin receptor function on cells, the data base of shifts in the curves shown in FIG. 7 will enable diagnosticians to immediately identify persons showing early stages of maturity on set diabetes.

It will be appreciated that the instant specification and claims are set forth by way of illustration and not limitation, and that various modifications and changes may be made without departing from the spirit and scope of the present invention.

What is claimed is:

1. A diagnostic method for clamping the blood glucose concentration of a subject at any one of a plurality of levels, comprising the steps of: selecting a desired clamping level (BC); periodically determining the value of the present blood glucose concentration (GY) in the bloodstream of the subject; and introducing dextrose into the bloodstream of the subject at a rate (DR) derived in accordance with $$DR = WT\left[\left(\frac{BC - GY}{3 + M}\right)KS + RC\right]$$

wherein:
DR = dextrose infusion rate for clamp (mg/min)
WT = body weight (kg)
BC = desired clamp level (mg %)
GY = present blood glucose level, corrected to fit a least squares regression line (mg %)
M = slope of the least squares regression line fit for the last five glucose values
KS = constant to allow adjustment for differences in metabolism $$RC = .9RC_{Last} + .1\left(\frac{DR_{Last}}{WT}\right)$$

(Glucose utilization in mg/kg/min).

2. The method according to claim 1, further comprising the step of introducing insulin into the bloodstream of the subject at a rate $$IR = RL \times WT$$

wherein:
IR = insulin infusion rate (mU/min)
RL = selected rate of insulin loading per kg of body weight.

3. The method according to claim 2, further comprising introducing insulin into the bloodstream at a plurality of selected different fixed rates (IR) for a normoglycemic clamp level (BC) and determining the steady state value of the dextrose infusion rate (DR) for each insulin infusion rate.

* * * * *